United States Patent
Pigg et al.

(10) Patent No.: US 10,758,423 B2
(45) Date of Patent: Sep. 1, 2020

(54) HYDROGEL WOUND DRESSINGS EXHIBITING REDUCED FIBER LOSSES IN USE

(71) Applicant: KCI USA, INC., San Antonio, TX (US)

(72) Inventors: William Pigg, Elvington (GB); Margaret Stedman, Harrogate (GB); Deborah Addison, Via (GB); Simon William Bayliff, Skipton (GB); Breda Mary Cullen, Skipton (GB); Paul Howard Lowing, Keighley (GB); Michelle Delbono, Earby (GB)

(73) Assignee: KCI USA, INC., San Antonio, TX (US)

( * ) Notice: Subject to any disclaimer, the term of this patent is extended or adjusted under 35 U.S.C. 154(b) by 792 days.

(21) Appl. No.: 15/411,873

(22) Filed: Jan. 20, 2017

(65) Prior Publication Data

US 2017/0128614 A1 May 11, 2017

Related U.S. Application Data (63) Continuation of application No. 12/373,619, filed as application No. PCT/GB2007/002616 on Jul. 12, 2007, now Pat. No. 9,579,411.

(30) Foreign Application Priority Data

Jul. 13, 2006 (GB) .................................. 0613939.8

(51) Int. Cl.
*A61F 13/00* (2006.01)
*A61L 15/60* (2006.01)
(Continued)

(52) U.S. Cl.
CPC .. *A61F 13/00063* (2013.01); *A61F 13/00012* (2013.01); *A61F 13/00017* (2013.01);
(Continued)

(58) Field of Classification Search
CPC ............ A61F 13/0008; A61F 13/00017; A61F 13/00063; A61F 2013/00217–00234
See application file for complete search history.

(56) References Cited

U.S. PATENT DOCUMENTS

| 778,813 A | 12/1904 | Taylor |
| 1,355,846 A | 10/1920 | Rannells |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Would Control and Treatment: Clinical Experience; Annals of Plastic Surgery.
(Continued)

*Primary Examiner* — Susan S Su
(74) *Attorney, Agent, or Firm* — Foley & Lardner LLP (57) ABSTRACT

A wound dressing comprising: a water-absorbent fabric comprising at least about 10 wt. % of hydrogel-forming absorbent fibers based on the dry weight of the fabric; and an adhesion-resistant, water-permeable wound contacting surface textile layer that is substantially continuously bonded to at least one surface of said fabric. The surface textile layer may be formed by surface treatment of the fabric, or by bonding a suitable textile web to the surface of the fabric.

22 Claims, 3 Drawing Sheets

(51) Int. Cl.
*A61L 15/28* (2006.01)
*A61L 15/18* (2006.01)

(52) U.S. Cl.
CPC ........ *A61F 13/00029* (2013.01); *A61L 15/18* (2013.01); *A61L 15/28* (2013.01); *A61L 15/60* (2013.01); *A61F 2013/00217* (2013.01); *A61L 2300/404* (2013.01)

(56) References Cited

U.S. PATENT DOCUMENTS

| | | | |
|---|---|---|---|
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A * | 2/1983 | Errede .............. A61F 13/00046 128/DIG. 21 |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,867,150 | A * | 9/1989 | Gilbert .............. A61F 13/0206 602/47 |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,197,945 | A * | 3/1993 | Cole .............. A61F 13/00008 28/105 |
| 5,215,522 | A | 6/1993 | Page et al. |
| 5,218,973 | A * | 6/1993 | Weaver .............. A61B 5/0408 607/152 |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,340,363 | A * | 8/1994 | Fabo .............. A61F 13/00063 424/446 |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,080,420 | A * | 6/2000 | Qin .............. A61L 15/225 424/443 |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,471,982 | B1* | 10/2002 | Lydon .............. A61L 15/225 424/443 |
| 6,488,643 | B1 | 12/2002 | Tumey et al. |
| 6,493,568 | B1 | 12/2002 | Bell et al. |
| 6,548,730 | B1* | 4/2003 | Patel .............. A61L 15/28 602/41 |
| 6,553,998 | B2 | 4/2003 | Heaton et al. |
| 6,814,079 | B2 | 11/2004 | Heaton et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2003/0040691 | A1* | 2/2003 | Griesbach, III .... A61F 13/0273 602/45 |
| 2003/0176827 | A1* | 9/2003 | Chandra .............. A61L 15/18 602/48 |
| 2005/0054998 | A1 | 3/2005 | Poccia et al. |
| 2005/0056292 | A1* | 3/2005 | Cooper .............. A61B 17/22 128/898 |
| 2007/0166399 | A1* | 7/2007 | Burton .............. A01N 59/16 424/618 |
| 2008/0312572 | A1* | 12/2008 | Riesinger .......... A61F 13/00008 602/43 |
| 2009/0156974 | A1* | 6/2009 | Truelsen .............. A61F 13/022 602/45 |
| 2010/0291184 | A1* | 11/2010 | Clark .............. A61F 13/0203 424/445 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| DE | 4407031 | 9/1995 |
| EP | 0100148 A1 | 2/1984 |

(56) References Cited

FOREIGN PATENT DOCUMENTS

| | | | |
|---|---|---|---|
| EP | 0117632 A2 | 9/1984 | |
| EP | 0161865 A2 | 11/1985 | |
| EP | 0251810 | 1/1988 | |
| EP | 0358302 A2 | 3/1990 | |
| EP | 0450671 | 10/1991 | |
| EP | 0275353 | 7/1998 | |
| EP | 1018967 A1 | 7/2000 | |
| GB | 692578 A | 6/1953 | |
| GB | 1430634 | 3/1976 | |
| GB | 2074029 A * | 10/1981 | ............ A61L 15/06 |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4263855 | 9/1992 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | 2003053584 | 7/2003 | |
| WO | 2006020213 | 2/2006 | |
| WO | 200800701 | 1/2008 | |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986; pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological arid Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007

International Search Report and Written Opinion; International Application No. PCT/GB2007/002616; International Filing Date Jul. 12, 2007; 9 pages.

\* cited by examiner

HYDROGEL WOUND DRESSINGS EXHIBITING REDUCED FIBER LOSSES IN USE

The present invention relates to wound dressings comprising hydrogel-forming absorbent fibers, wherein the dressings exhibit reduced fiber loss into wounds daring use.

Wound dressings are known that comprise a wound contacting layer in the form of a nonwoven fabric comprising hydrogel-forming absorbent fibers. Typical hydrogel-forming absorbent fibers include polyacrylates calcium alginate and sodium carboxymethylcellulose (NaCMC) fibers. These fibers absorb several times their own weight of wound fluid, and form a hydrogel with swelling. Alginate in particular also has a positive therapeutic effect on wound healing. However, most of these hydrogel-forming fibrous materials are not absorbed completely a in vivo, and therefore it is desirable to avoid shedding of these fibers into the wound under treatment.

It is known to provide wound dressing materials in the form of a nonwoven fabric made up of a mixture of hydrogel-forming absorbent fibers and non-absorbent textile fibers, such as polyamide staple fibers. The non-absorbent textile fibers provide improved structural integrity and improved wicking properties to the fabric. However, the shedding of these non-absorbent textile fibers into wounds under treatment is also undesirable, since most of the textile fibers are not absorbable in vivo.

WO03/053534 describes wound dressing materials in the form of a nonwoven fabric made up of a mixture of hydrogel-forming absorbent fibers and non-absorbent textile fibers, in which some of the non-absorbent textile fibers are coated with silver to give the dressings antimicrobial properties. The silver-coated fibers have a dark color, and it is especially desirable to avoid shedding of these fibers into the wound under treatment because of the undesirable appearance of the dark fibers in the wound.

The shedding of fibers from a nonwoven textile layer into a wound can be reduced by providing a suitable top sheet (wound contacting sheet) over the textile layer in the wound dressing. For example, a top sheet in the form of a polymer film having apertures much smaller than the length of the textile fibers can be used as the top sheet. EP-A-0275353 describes dressings of this type comprising a top sheet formed of an elastomeric, soft, non-absorbent polyurethane film less than 50 micrometers thick, thermally bonded to a surface of the absorbent textile wound dressing, each perforation in the film having open areas equal to a circle having a diameter of 0.25 to 1.2 mm, the perforations being present in sufficient number, and so distributed, as to provide an open area in the range from 5% to 25% of the total area of the film.

However, the use of a separate top sheet reduces the therapeutic effectiveness of the hydrogel forming fibers and of the antimicrobial silver in the textile dressing, and also interferes with uptake of wound fluid from the wound and reduces conformability of the dressing.

It has now been found that the shedding of fibers from hydrogel textile dressings into a wound can be reduced by bonding a thin layer of an adhesion-resistant material directly to the wound facing surface of the hydrogel-containing fabric.

Accordingly, in a first aspect the present invention provides a wound dressing comprising: a water-absorbent fabric, wherein said fabric has dry basis weight of at least about 100 g/m$^2$ and comprises at least about 10 wt. % of hydrogel-forming absorbent fibers based on the dry weight of the fabric; and an adhesion-resistant, water-permeable wound contacting textile surface layer that is substantially continuously bonded to at least one surface of said fabric. Suitably, the fabric comprises at least about 20 wt. % of the hydrogel-forming fibers, for example from about 30 wt. % to about 50 wt. % of such fibers.

The term "hydrogel-forming fibers" refers to fibers that can absorb at least about twice their own weight of water, preferably at least about four times their own weight of water, to form a hydrogel. The fibers are normally insoluble in water. Suitable materials for the hydrogel-forming fibers include alginates, carboxymethylcelluloses, hydroxyethylcelluloses, polyacrylates, and hyaluronates. Preferred materials are calcium alginate and sodium carboxymethylcellulose and mixtures thereof.

Suitably, the fabric comprises at least about 10 wt. % based on the dry weight of the fabric of substantially non-water-absorbent textile fibers, and preferably it comprises at lesat about 20 wt. % of such fibers, for example from about 30 wt. % to about 60 wt. % of such fibers. Suitable non-absorbent textile fibers include polyamide fibers such as nylon fibers, polyolefin fibers, and viscose fibers.

Suitably, the fabric comprises (and may consist essentially of) a mixture of hydrogel-forming fibers and substantially non-absorbent textile fibers, wherein at least a fraction of the fibers are coated with silver to provide antimicrobial activity. Preferably, the silver coating is applied to the non-absorbent textile fibers. The term "fibers" herein generally refers to staple fibers, but it may refer to longer textile fibers. It does not refer to pulp fibers. In any case, the median length of the fibers used to form the fabric is generally at least about 10 mm. Suitably, the amount of silver in the fabric is from about 0.1% to about 10 wt. % based on the dry weight of the fabric.

In certain embodiments, the adhesion-resistant textile surface layer has been formed by treating a surface layer of the web with a lubricant. That is to say, the fibers in the surface layer have the same composition as the body of the textile layer and form part of the same fabric, but are coated with a lubricant composition. The lubricant may be applied in solution in a suitable solvent, for example by spraying, and then dried. The lubricant penetrates only a short distance into the surface of the fabric layer, whereby it coats fibers near the s of the fabric layer but not in the core of the fabric layer. In this way the lubricant significantly alter the absorbency or the porosity of the fabric.

The amount of lubricant that is a plied in these embodiments is small. Typical amounts of dry lubricant per side of the fabric are from about 0.1 g/m$^2$ to about 20 g/m$^2$, preferably from about 0.5 g/m$^2$ to about 10 g/m$^2$, for example from about 1 g/m$^2$ to about 4 g/m$^2$.

The term "lubricant" refers generally to any substance that reduces the adherency of the fabric to the wound tissue. Generally, the lubricant is mot soluble in water so that it is not washed off in the wound. Suitably, the lubricant comprises a silicone compound. Suitable silicone compounds comprise polyalkylsiloxanes, in particular polydimethylsiloxanes. In certain embodiments, the lubricant may be polymerised or cross-linked in situ. Other suitable lubricants are fluorocarbon compounds, for example perfluoroalkanes such as polytetrafluoroethylene (PTFE).

In other embodiments, the lubricant comprises a substance selected from the group consisting of medically acceptable lipids, mineral oils and waxes, and mixtures thereof. Suitably, the lubricant is hydrophobic. It has been found that the use of a hydrophobic lubricant gives enhanced fiber retention, without significantly reducing the rate or quantity of liquid that is absorbed by the dressing.

In other embodiments, the lubricant comprises a medically acceptable lubricating polymer. Preferred polymers are biopolymers such as collagen, gelatin, cellulose derivatives such as oxidized regenerated cellulose (ORC), and starch derivatives. In certain embodiments the polymer may be a mucopolysaccharide, for example hyaluronic acid (HA). HA functions in nature as a lubricant in joint fluid.

It is known from DE-A-4407031 to apply silicones as a hydrophobic surface finish on conventional fabrics for use in wound dressings. However, silicone coatings have not hitherto been suggested to reduce fiber loss from hydrogel absorbent fabrics.

JP-A-4263855 describes antimicrobial wound dressings comprising a thin layer of a hydrogel that is coated with a hydrophobic silicone material. The purpose of the hydrogel is to maintain adequate humidity at the wound surface.

In alternative embodiments, the adhesion resistant surface textile layer comprises a non-adherent textile web having a basis weight of from about 2 to about 100 g/m2 that is directly bonded to the surface of the fabric. The composition of the fibers making up the textile web is different from that of the fibers making up the absorbent fabric. In particular, the surface textile web generally does not comprise any gel-forming fibers.

The surface textile web may be a woven or knitted fabric, but it is preferably a nonwoven fabric, more preferably a thermally-bonded nonwoven fabric comprising thermoplastic fibers. Examples of suitable thermoplastic fibers include polyamide, polyester and polypropylene. A woven or knitted or non-bonded nonwoven textile preferably consists of continuous filament yarn to minimise the possibility of textile fibers becoming detached and remaining behind on removal from a wound. Other types of nonwoven fabric may also advantageously consist of continuous filament yarn; in particular, a thermally spunbonded fabric may be used. The basis weight of the surface textile layer is preferably in the range from 5 to 80, more preferably from 10 to 50, g/m$^2$. The surface textile layer should be suitable for medical applications, and be susceptible to conventional sterilisation procedures such as exposure to ethylene oxide or to electron beam or gamma-ray irradiation.

Suitably, the non-adherent surface textile web comprises thermoplastic fibers, and the surface textile layer has been bonded to the water-absorbent fabric by thermal bonding, such as melt bonding, optionally also with compression.

In certain embodiments, the non-adherent surface textile web may comprise fibers that have been coated with a non-adherent composition prior to lamination with the absorbent fabric. The non-adherent composition may be a lubricant as hereinbefore described. For example, the web may be a gauze coated with a paraffinic material (so-called "tulle grass"). Suitable webs include cellulose acetate fabrics coated with petrolatum, such as those available from Johnson & Johnson under the Registered Trade Mark ADAPTIC. Other suitable webs include viscose fabrics coated with silicone, such as those available from Johnson & Johnson under the Registered Trade Mark N-A ULTRA.

Suitably, the wound dressing according to the present invention is sterile and packaged in a microorganism-impermeable container.

Specific embodiments of the present invention will now be described further, by way of example, with reference to the accompanying drawings, in which.

Figure 1:
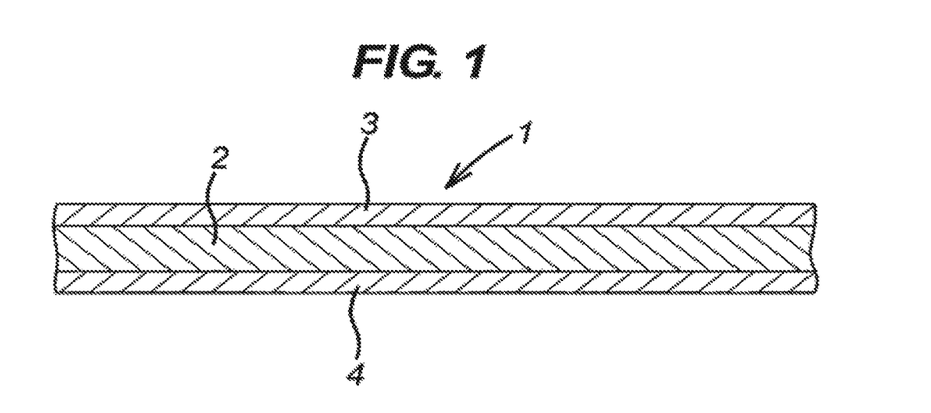
FIG. 1 shows a schematic cross-section through a wound dressing according to the present invention.

Referring to FIG. 1, the dressing 1 comprises fabric layer 2 containing hydrogel-forming fibers and non-absorbent textile fibers, some of which are coated with metallic silver. The dressing further comprises adhesion-resistant nonwoven textile webs 3,4 (the thickness of which is exaggerated in the Figure) continuously bonded over the upper and lower surfaces of the fabric layer 2.

EXAMPLE 1

The fabric layer is at calcium alginate needled felt dressing incorporating silver-coated nylon fibers. The composition is as follows: calcium alginate and carboxymethyl cellulose (CMC) fibers 60% and silver coated nylon 40%. The basis weight of the fabric layer is about 150 g/m$^2$, and the uncompressed thickness of the fabric layer is about 2 mm. The fabric layer is commercially available from Johnson & Johnson under the Registered Trade Mark SILVERCEL.

The adhesion-resistant non woven web is formed from a layer of M1590 heat laminating material obtained from Freudenberg Vliesstoffe KG. It comprises 80% of an aliphatic non-cyclic co-polyamide (6/66.6/12-copolyamide, CAS number 26777-62-8), and 20% of polyetherester block copolyamide in which the polyetherester comprises a polyether block of medium molecular weight and the polyamide block is aliphatic acid non-cyclic. The basis weight of the web is only about 10 g/m$^2$. This gives the layer a high porosity for water uptake from the wound.

The nonwoven web 2 was bonded to the fabric layer 1 by heating and compression. Suitable conditions are 116-127° C., press time 10-14 seconds, and pressure 150-300 kPa.

EXAMPLE 2

A dressing according to the invention was prepared as described in Example 1, except that bonding of the textile surface layer to the fabric body was achieved without compression, by placing the laminate in an oven at 150° C. for 10 minutes.

EXAMPLE 3

A dressing according to the invention was prepared as described in Example 2, except that the textile surface layer had a basis weight of 20 g/m$^2$.

EXAMPLES 4-10

Silicone-coated hydrogel fiber fabrics were prepared from a SILVERCEL fabric containing hydrogel-forming fibers as described in Example 1.

The silicone coating was made by first mixing together the two silicone components (SILOPREN RTV 2K Gel AC3293 components A and B supplied by GE BAYER) and then dissolving the mixture in acetone to assist spraying. Acetone concentration was 20-35% based on the weight of the mixture (hexane can also be used). The silicone coating was applied to both sides of the fabric in the following amounts (total dry weight of silicone—i.e. divide by two for the coating density per side of the fabric):

| | |
|---|---|
| Example 4 | 4 g/m² |
| Example 5 | 8 g/m² |
| Example 6 | 14 g/m² |
| Example 7 | 20 g/m² |
| Example 8 | 21 g/m² |
| Example 9 | 24 g/m² |
| Example 10 | 26 g/m² |

EXAMPLES 11-12

Lubricant-coated hydrogel fiber fabrics were prepared from a SILVERCEL fabric containing hydrogel-forming fibers as described in Example 1 by spraying the surfaces of the fabric with a medically acceptable mineral oil. Two different coating weights were used.

EXAMPLE 13

A lubricant-coated hydrogel fiber fabric was prepared from a SILVERCEL fabric containing hydrogel-forming fibers as described in Example 1 by spraying the surfaces of the fabric with a solution of Hyaluronic acid.

REFERENCE EXAMPLE 1

Measurements of fiber loss, adherency and absorbency as detailed below were also carried out on a reference sample of SILVERCEL fabric as described in Example 1, without any coating.

REFERENCE EXAMPLE 2

Measurements of adherency and absorbency as detailed below were also carried out on a reference sample of AQUACEL Ag fabric supplied by, AQUACEL Ag is a needle-bonded nonwoven fabric formed from carboxymethylcellulose gel-forming fibers and containing silver in ionic form bonded to the CMC. There is no coating on the surfaces of the fabric.

REFERENCE EXAMPLE 3

Measurements of adherency and absorbency as detailed below were also carried out on a reference sample of a wound dressing made by heat-bonding a vacuum-perforated ethylene methyl acrylate (EMA) film onto the surfaces of a fabric layer as described in Example 1. The characteristics of the EMA film were as described in EP-A-1168998, the entire content of which is incorporated herein by reference. The lamination was performed at about 150° C., between sheets of siliconized release paper.

REFERENCE EXAMPLE 4

Measurements of adherency and absorbency as detailed below were also carried out on a reference sample of a wound dressing made by heat-bonding a thermoplastic net of base weight 10-88 g/m2, hole size 100-1400 micrometers a and thickness 0.05-0.3 mm obtained from Delstar Technologies Inc. of Bristol, UK onto the surfaces of a fabric layer as described in Example 1. The lamination was performed at about 150° C., between sheets of siliconized release paper.

Procedure 1

A qualitative assessment of fiber loss was performed by applying adhesive tape to the surface of the dressing the adhesive side down at an applied pressure of about 5 g/cm2, followed by lifting the tape from the dressing and observing the amount of fiber attached to the tape. It was found that fiber shedding onto the tape of dressing of Example 1 was very much less than that observed with Reference Example 1.

Procedure 2

A Fibrin Clot Adhesion Test used as an in-vitro method to evaluate likely fiber loss to the wound surface. A fibrin clot is formed from bovine plasma fibrinogen, phosphate buffered saline, bovine serum albumin and bovine thrombin. The formed clot is placed between samples of the dressing, dried and pulled apart in an Instron force measurement device. The force required to pull the dressings apart is measured.

Figure 2:
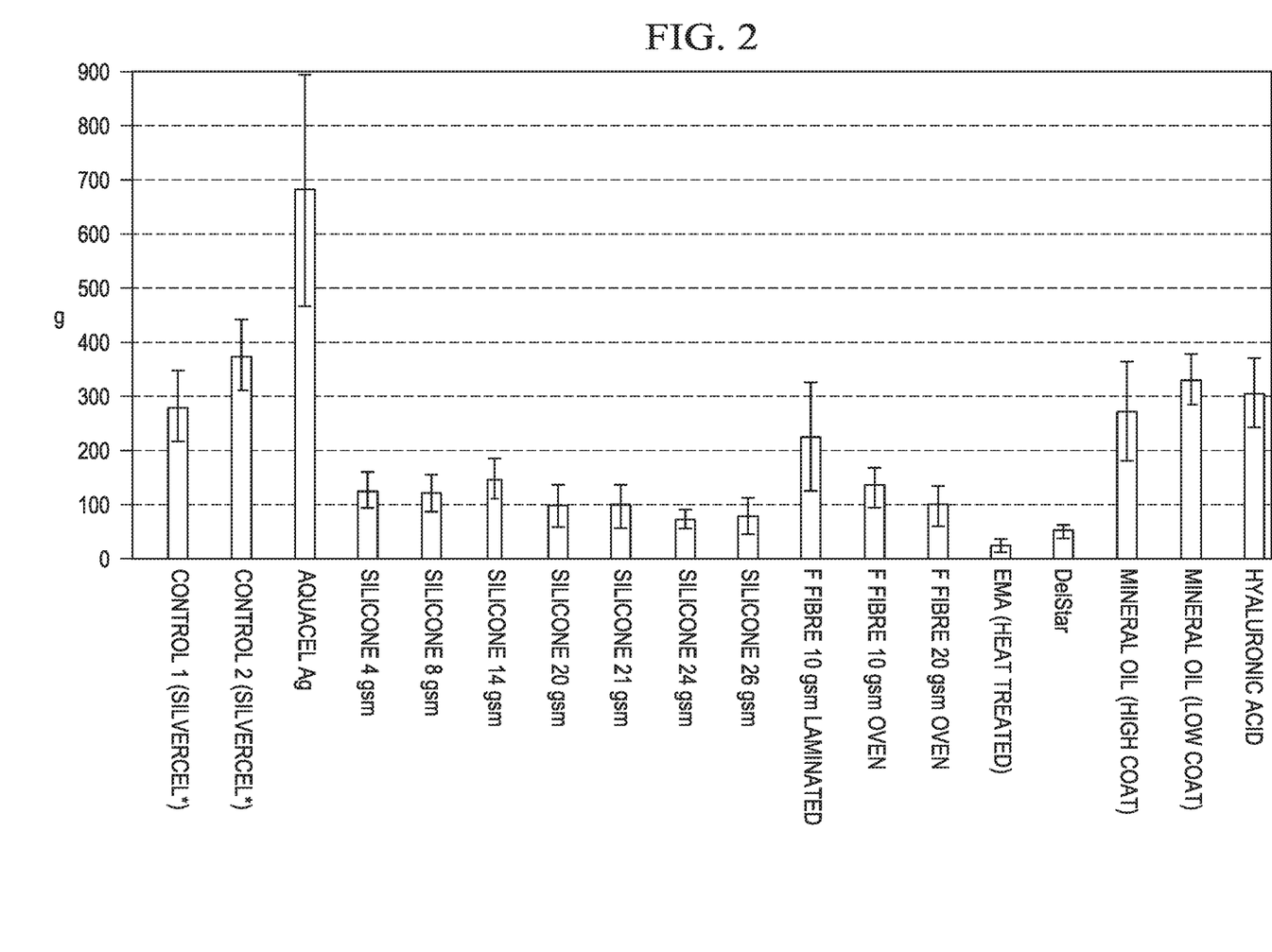
FIG. 2 shows a bar chart of measured peak fibrin clot adhesion force for wound dressings according to the invention and for certain reference dressings.

The peak force required to pull the dressings apart is shown graphically in FIG. 2 for the above Examples. It can be seen that all of the examples exhibit a reduced fibrin clot adhesion force. The effect is especially marked for the siliconized samples. The effect is observed down to very low coating weights of the silicone composition.

Procedure 3

The wound fluid absorbency of the example dressings was evaluated as follows. The method was based on the absorbency test on Alginate dressings described in the British Pharmacopoeia 1993, Addendum 1995, Page 1706.

Figure 3:
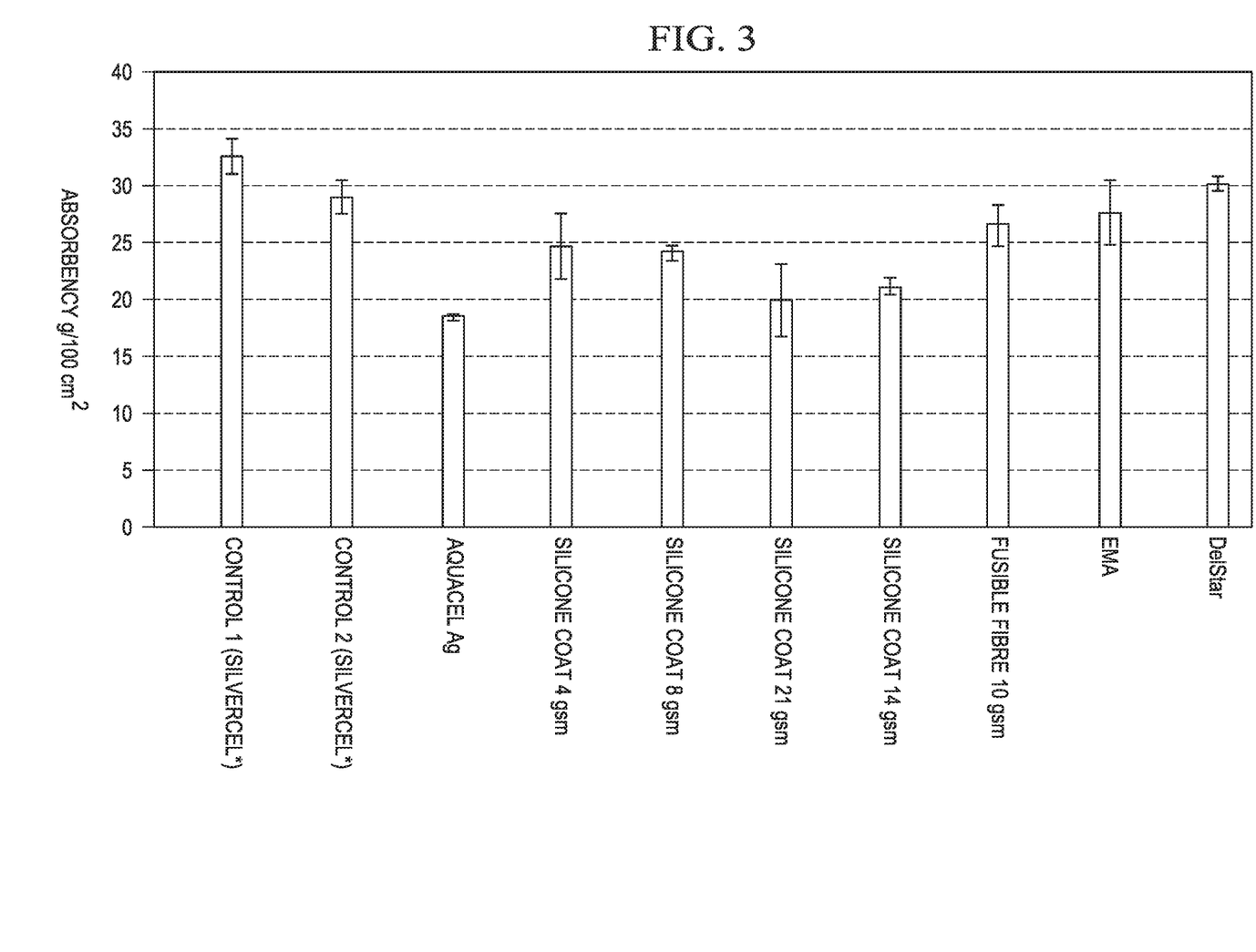
FIG. 3 shows a bar chart of measured liquid absorbency for and dressings according to the invention and for certain reference dressings.

Briefly, a 5 cm×5 cm sample was excised form a dressing and weighed. This sample was placed in a Petri dish. The sample is then submerged in a solution of sodium chloride and calcium for chloride that had been heated to 37° C. The material was suspended for 30 seconds using a set of forceps before the sample was weighed. This test was repeated on a further 4 samples. The absorbency was then expressed as the age weight of solution retained per 100 cm². The results are shown in FIG. 3. It can be seen that the dressings according to the invention all have absorbency similar to that of the unmodified SILVERCEL dressings.

Procedure 4

The silver release into simulated wound fluid at 37° C. over a period of 3 days of the dressings according to the above examples was evaluated as follows.

The simulated wound fluid was a solution containing:

The wound dressings wee tested over days. At each 24 hour time-point, the dressings were re-challenged with a fresh amount of simulated wound fluid equivalent to 5 ml/2.5×2.5 cm. Each batch was analysed in triplicate.

Analysis was perfumed against a silver standard curve prepared in simulated wound fluid was carried out using the Perkin Elmer AAnalyst 200 Atomic Absorption Spectrometer Standards of known concentration were prepared in the same simulated wound fluid as used for the dressings. Calibration curves were prepared daily.

The results showed that the dressings according to the present invention gave substantially the same rate and amount of silver release as the untreated SILVERCEL dressings.

The above embodiments have been described for the purpose of illustration only. Many other embodiments falling within the scope of the present invention will be apparent to the skilled reader.

The invention claimed is:

1. A wound dressing, comprising:
   an absorbent layer comprising an absorbent material and a plurality of non-absorbent silver-coated fibers; and
   a wound-contacting layer comprising a non-adherent, moisture-permeable textile material, wherein the wound-contacting layer is positioned on a first surface of the absorbent layer.

2. The wound dressing of claim 1, wherein the absorbent layer comprises a non-woven pad.

3. The wound dressing of claim 1, wherein the absorbent material comprises a plurality of hydrogel-forming fibers comprising an alginate.

4. The wound dressing of claim 1, wherein the absorbent material comprises a plurality of hydrogel-forming fibers comprising a carboxymethylcellulose (CMC).

5. The wound dressing of claim 1, wherein the plurality of non-absorbent silver-coated fibers comprises polyamide fibers.

6. The wound dressing of claim 1, wherein the plurality of non-absorbent silver-coated fibers comprise silver-coated nylon fibers.

7. The wound dressing of claim 1, wherein the wound-contacting layer is laminated to the first surface of the absorbent layer.

8. The wound dressing of claim 1, further comprising a backing layer comprising the non-adherent material and positioned on a second surface of the absorbent layer.

9. The wound dressing of claim 1, wherein the wound-contacting layer comprises a textile layer that is substantially continuously bonded to the first surface of the absorbent layer.

10. The wound dressing of claim 1, wherein the absorbent material of the absorbent layer comprises a plurality of hydrogel-forming absorbent fibers.

11. The wound dressing of claim 1, wherein the absorbent material comprises at least 10 wt. % of hydrogel-forming absorbent fibers based on the dry weight of the absorbent layer.

12. The wound dressing of claim 1, wherein the absorbent layer comprises at least 10 wt. % of the non-absorbent silver-coated fibers based on the dry weight of the absorbent layer.

13. The wound dressing of claim 1, wherein:
   the absorbent material comprises a plurality of hydrogel-forming fibers; and
   a median length of the hydrogel-forming fibers and the non-absorbent silver-coated fibers is at least 10 millimeters (mm).

14. The wound dressing of claim 1, wherein the absorbent material comprises a plurality of hydrogel-forming fibers comprising a hyaluronate.

15. The wound dressing of claim 1, wherein the absorbent material comprises a plurality of hydrogel-forming fibers comprising a polyacrylate.

16. A wound dressing material, comprising:
   a non-woven absorbent pad comprising an alginate material and a plurality of silver-coated nylon fibers; and
   a non-adherent wound contact layer laminated to a first surface of the non-woven absorbent pad.

17. The wound dressing material of claim 16, wherein the non-woven absorbent pad further comprises a carboxymethylcellulose (CMC).

18. The wound dressing material of claim 16, wherein the alginate material comprises calcium alginate.

19. The wound dressing material of claim 17, wherein the carboxymethylcellulose (CMC) comprises sodium carboxymethylcellulose.

20. The wound dressing material of claim 16, wherein the non-adherent wound contact layer comprises a moisture-permeable textile material.

21. The wound dressing material of claim 16, wherein the non-adherent wound contact layer comprises a surface layer treated with a lubricant.

22. The wound dressing material of claim 21, wherein the lubricant comprises a silicone compound.

* * * * *